(12) United States Patent
Chen et al.

(10) Patent No.: US 9,518,275 B2
(45) Date of Patent: Dec. 13, 2016

(54) METHOD FOR DECREASING PYRUVATE CATABOLISM AND INCREASING THE ACCUMULATION OF PYRUVATE IN MICROBES

(71) Applicants: Jian Chen, Wuxi (CN); Jingwen Zhou, Wuxi (CN); Hongwei Guo, Wuxi (CN); Yongkun Lv, Wuxi (CN); Guocheng Du, Wuxi (CN)

(72) Inventors: Jian Chen, Wuxi (CN); Jingwen Zhou, Wuxi (CN); Hongwei Guo, Wuxi (CN); Yongkun Lv, Wuxi (CN); Guocheng Du, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 17 days.

(21) Appl. No.: 14/583,260

(22) Filed: Dec. 26, 2014

(65) Prior Publication Data

US 2016/0138054 A1    May 19, 2016

(30) Foreign Application Priority Data

Nov. 19, 2014   (CN) .......................... 2014 1 0665313

(51) Int. Cl.
| | | |
|---|---|---|
| *C12N 1/20* | (2006.01) |
| *C12P 7/40* | (2006.01) |
| *C12N 9/10* | (2006.01) |
| *C12N 1/16* | (2006.01) |

(52) U.S. Cl.
CPC . *C12P 7/40* (2013.01); *C12N 1/16* (2013.01); *C12N 9/1029* (2013.01); *C12Y 203/01012* (2013.01)

(58) Field of Classification Search
CPC ........................... C12P 7/40; C12Y 203/01012
USPC ............................................... 435/136, 254.2
See application file for complete search history.

(56) References Cited

U.S. PATENT DOCUMENTS

2016/0138054 A1* 5/2016 Chen .......................... C12P 7/40
                                                                    435/136

* cited by examiner

*Primary Examiner* — Tekchand Saidha
(74) *Attorney, Agent, or Firm* — Lili Chen

(57) ABSTRACT

The present invention provides a method for decreasing pyruvate catabolism and increasing the accumulation of pyruvate in microbes. By overexpressing wild type dihydrolipoamide acetyltransferase or dihydrolipoamide acetyltransferase mutants which have mutations at conservative active sites, the present invention provide a method to decrease overall activity of pyruvate dehydrogenase complex and pyruvate catabolism, and thus increase the accumulation of extracellular pyruvate without killing the pyruvate-producing microbes. Overexpressing dihydrolipoamide acetyltransferase mutants is an effective way to increase pyruvate accumulation.

9 Claims, 4 Drawing Sheets

METHOD FOR DECREASING PYRUVATE CATABOLISM AND INCREASING THE ACCUMULATION OF PYRUVATE IN MICROBES

CROSS-REFERENCES AND RELATED APPLICATIONS

This application claims the benefit of priority to Chinese Application No. 201410665313.9, entitled "A Method for Weakening Pyruvate Catabolism and Improving the Accumulation of Pyruvate in Microbes", filed Nov. 19, 2014, which is herein incorporated by reference in its entirety.

BACKGROUND OF THE INVENTION

Field of the Invention

The present invention relates to the field of metabolic engineering, and more particularly relates to a method for weakening pyruvate catabolism and improving the accumulation of pyruvate in microbes.

Description of the Related Art

Pyruvate (Pyruvic acid) is one of the important intermediates in the tricarboxylic acid cycle (TCA cycle). It not only plays a key role in microbial metabolisms, such as energy metabolism and synthesis of amino acids, proteins and vitamins, but also occupies the key regulation point of TCA cycle. Compared with the other intermediates in the TCA cycle, regulations for pyruvate metabolism are much more complicated.

As an essential intermediate in fine chemicals and pharmaceutical industry, pyruvic acid is widely used in the synthesis of amino acids, vitamins and other organic molecules. It also has a wide range of applications in pharmaceutics, organic synthesis and nutritional supplement synthesis. In order to meet the rising market demand, more effective methods for synthesizing pyruvic acid are needed.

There are many problems, such as poor efficiency and low yield, when producing pyruvic acid using microbes. Genetic modification is necessary for high level productivity. However, to those obligated aerobes, pyruvic acid is at the key position of the energy supply chain. It may cause side effects to cell growth even death if genes of the central metabolic pathway are knocked out. Particularly, pyruvate producing yeast cells belong to obligate aerobic microorganism, and genomic deletion of key enzymes in TCA cycle pathways could be lethal. The present invention provides a method to decrease the catabolism of pyruvate and thus increase the accumulation of pyruvate in microbes while avoiding lethal effects caused by modification of key TCA components in the engineered microbes.

DETAILED DESCRIPTION

The goal of the present invention is to provide a method for decreasing pyruvate catabolism and increasing the accumulation of pyruvate in microbes via overexpression of wild-type dihydrolipoamide acetyltransferase or mutants of dihydrolipoamide acetyltransferase. As the pyruvate dehydrogenase activity is reduced in the recombinant strains, pyruvate catabolism is decreased, thus increasing the accumulation of the carboxylate.

In a preferred embodiment, the parental strain is yeast or the other fungus.

In a preferred embodiment, overexpression of dihydrolipoamide acetyltransferase alters the endogenous stoichiometric equilibration of the pyruvate dehydrogenase complex. The increase of dihydrolipoamide acetyltransferase interferes with the balanced assembly of pyruvate dehydrogenase, dihydrolipoamide dehydrogenase and dihydrolipoamide acetyltransferase in the pyruvate dehydrogenase complex, resulting in decreased overall activity of pyruvate dehydrogenase complex in the cells. Decreasing the overall activity of pyruvate dehydrogenase complex leads to less catabolism and more accumulation of pyruvate.

In a preferred embodiment, overexpression of mutants of dihydrolipoamide acetyltransferase, of which the conservative active site residue Histidine (His) or Aspartate (Asp) is mutated into Alanine (Ala), interferes the normal assembly of the pyruvate dehydrogenase complex and reduces the activity of dihydrolipoamide acetyltransferase. This results in the reduced intracellular overall activity of pyruvate dehydrogenase complex and thus increased accumulation of pyruvate.

In a preferred embodiment, the host cell is *Yarrowia lipolytica* (*Y. lipolytica*). The amino acid sequence of the wild-type dihydrolipoamide acetyltransferase from *Y. lipolytica* is set forth in SEQ ID NO.1. The conservative active site residue of the enzyme, His 409 or Asp 413, is mutated into Ala to get mutant H409A or D413A, respectively.

In a preferred embodiment, the host cell is *Torulopsis glabrata* (*T. glabrata*). The amino acid sequence of the wild-type dihydrolipoamide acetyltransferase from *T. glabrata* is set forth in SEQ ID NO: 2. The conservative active site residue of the enzyme, His 442 or Asp 446, is mutated into Ala to get mutant H442A or D446A, respectively.

The present invention also provides a series of recombinant *Y. lipolytica* derived from *Y. lipolytica* WSH-Z06 CCTCC NO: M20714, in which wild-type dihydrolipoamide acetyltransferase or its mutants is overexpressed.

The recombinant *Y. lipolytica* can be constructed as follows:

(1) Constructing the integrative expression vector: the amplified open reading frame (ORF) of hph encoding hygromycin phosphotransferase and plasmid p0 are digested using restriction enzyme Stu I and Hind III. The digested fragments are ligated to obtain integrative expression vector p0(hph).

(2) Constructing a recombinant expression plasmid: the ORF of LAT1 encoding dihydrolipoamide acetyltransferase is synthesized; ORF of LAT1 and the integrative plasmid p0(hph) are digested by Bam HI and Eco RI simultaneously which is followed by the ligation of the digested fragments to obtain a recombinant expression plasmid p0(hph)-LAT1; Site-directed mutagenesis of conservative active site residue is accomplished using primers H409A-F (SEQ ID NO:4)/H409A-R (SEQ ID NO:5) and D413A-F (SEQ ID NO:6)/D413A-R (SEQ ID NO:7), respectively. The resulted plasmids are p0(hph)-409A and p0(hph)-413A, respectively.

(3) Transforming the recombinant expression plasmid into *Y. lipolytica* WSH-Z06: The recombinant expression plasmids are linearized and transformed into *Y. lipolytica* WSH-Z06 using electroporation method. Positive transformants *Y. lipolytica*-K, *Y. lipolytica*-409A and *Y. lipolytica*-413A, in which p0(hph)-LAT1, p0(hph)-409A and p0(hph)-413A are introduced into yeast cells, respectively, are screened and verified.

The method of constructing plasmid p0 is well documented in Swennen D, Paul M F, Vernis L, Beckerich J M, Fournier A, Gaillardin C. Secretion of active anti-Ras single-chain Fv antibody by the yeasts *Yarrowia lipolytica* and *Kluyveromyces lactis*. Microbiology-Sgm, 2002. 148: 41-50.

Compared with *Y. lipolytica* WSH-Z06, biomass of the three recombinants, *Y. lipolytica*-K, *Y. lipolytica*-409A and *Y. lipolytica*-413A, was reduced to 86.5%, 22.0% and 26.2%, respectively; intracellular pyruvate dehydrogenase activity was reduced by 13.5%, 35.2% and 32.2%, respectively; pyruvate accumulation was increased from 20.5 g·L$^{-1}$ to 24.5 g/L, 38.6 g·L$^{-1}$ and 39.9 g·L$^{-1}$ respectively.

The present invention provides a recombinant *T. glabrata* which derives from *T. glabrata* CCTCC M202019 Δura3 and overexpresses dihydrolipoamide acetyltransferase or its mutation.

The recombinant *T. glabrata* can be constructed as follows:

(1) Constructing a recombinant expression plasmid: Open reading frame (ORF) of the gene LAT1 encoding dihydrolipoamide acetyltransferase is synthesized based on the published nucleotide sequence by NCBI; LAT1 ORF and the integrative plasmid pRS306TEF1 are digested by restriction enzyme Spe I and Bam HI simultaneously which is followed by the ligation of the digested fragments to obtain a recombinant expression plasmid pRS306TEF1-LAT1. Site-directed mutagenesis of conservative active site residue is accomplished using primers H442A-F (SEQ ID NO:8)/H442A-R (SEQ ID NO:9) and D446A-F (SEQ ID NO:10)/D446A-R (SEQ ID NO:11). pRS306TEF1-LAT1 is used as template DNA to get recombinant expression plasmid pRS306TEF1-442A and pRS306TEF1-446A.

(2) Transforming the recombinant expression plasmid into *T. glabrata* CCTCC M202019 Δura3: the recombinant expression plasmid is linearized and transformed into *T. glabrata* CCTCC M202019 Δura3 using an electroporation method; Positive transformants *T. glabrata*-C, *T. glabrata*-442A and *T. glabrata*-446A, which overexpress dihydrolipoamide acetyltransferase wild type, H442A mutant and D446A mutant, respectively, are screened and verified.

Compared with *T. glabrata* CCTCC M202019 Δura3, biomass of the three recombinants, *T. glabrata*-C, *T. glabrata*-442A and *T. glabrata*-446A, was reduced to 81.5%, 30.2% and 36.3% respectively; intracellular pyruvate dehydrogenase activity was reduced by 21.2%, 48.2% and 51.8% respectively; pyruvate accumulation was increased from 49.4 g·L$^{-1}$ to 56.8 g/L, 68.6 g·L$^{-1}$ and 74.3 g·L$^{-1}$.

The present invention also provides a method for producing pyruvate using the genetically engineered strain. The genetically engineered strain overexpresses wild-type dihydrolipoamide acetyltransferase or the mutants of dihydrolipoamide acetyltransferase of which its conserved active site residues are mutated.

In a preferred embodiment, the host cells for constructing genetically engineered strain is *Y. lipolytica*, particularly *Y. lipolytica* WSH-Z06. The amino acid sequence of the wild-type dihydrolipoamide acetyltransferase from *Y. lipolytica* is shown as SEQ ID NO:1. With regard to the mutation, the conservative active site residue of wild-type enzyme, His 409 or Asp 413, was individually mutated into Ala to get mutant H409A or D413A, respectively. The genetically engineered *Y. lipolytica* is cultured as follows. The seed medium contains 20 g·L$^{-1}$ glucose, 10 g·L$^{-1}$ peptone, 1 g·L$^{-1}$ KH$_2$PO$_4$, 0.5 g·L$^{-1}$ MgSO$_4$.7H$_2$O, and is adjusted to pH 5.5; the fermentation medium contains 100 g·L$^{-1}$ glycerol, 3 g·L$^{-1}$ (NH$_4$)$_2$SO$_4$, 3 g·L$^{-1}$ KH$_2$PO$_4$, 1.2 g·L$^{-1}$ MgSO$_4$.7H$_2$O, 0.1 g·L$^{-1}$ K$_2$HPO$_4$, 0.5 g·L$^{-1}$ NaCl and 2×10$^{-7}$ g·L$^{-1}$ thiamine, and is adjusted to pH 5.0 and is then added with 20 g·L$^{-1}$ CaCO$_3$. The recombinant strain is inoculated to the seed culture medium at 28° C., 200 rpm, and cultured for 16-18 hours. 150 ml seed culture medium (10%) is inoculated into 1.5 Liter fermentation medium in a 3 Liter fermentor, cultured at 28° C., 200 rpm for 144 hours.

In a preferred embodiment, the host cells for constructing genetically engineered strain is *Torulopsis glabrata*, especially *T. glabrata* CCTCC M202019 Δura3. The amino acid sequence of the wild type dihydrolipoamide acetyltransferase from *T. glabrata* is shown as SEQ ID NO:2. With regard to the mutation, the conservative active site residue of wild type enzyme, His 442 or Asp 446, is individually mutated into Ala to get mutation H442A or D446A.

The genetically engineered *T. glabrata* is cultured as follows. The seed medium contains 20 g·L$^{-1}$ glucose, 10 g·L$^{-1}$ peptone, 1 g·L$^{-1}$ KH$_2$PO$_4$, 0.5 g·L$^{-1}$ MgSO$_4$.7H$_2$O, and is adjusted to pH 5.5; The fermentation medium contains 120 g·L$^{-1}$ glucose, 7 g·L$^{-1}$ NH$_4$Cl, 5 g·L$^{-1}$ KH$_2$PO$_4$, 0.8 g·L$^{-1}$ MgSO$_4$.7H$_2$O, 6 g·L$^{-1}$ sodium acetate, 4 mg·L$^{-1}$ niacin, 30 μg·L$^{-1}$ thiamine, 100 μg·L$^{-1}$ pyridoxine hydrochloride, 10 μg·L$^{-1}$ biotin, 50 μg·L$^{-1}$ riboflavin, and is adjusted to pH 5.0. Vitamins are added to the fermentation medium after they are sterilized by filtration. The recombinant *T. glabrata* is inoculated into 25 mL seed medium in a 250 mL triangular flasks, and cultured at 28° C., 200 rpm for 24 hours. The seed culture is inoculated at a ratio of 10% (v/v) into 1.5 Liter fermentation medium in a 3 Liter fermentation tank, and cultured at 30° C., 400 rpm with a ventilation rate of 4 vvm for 80 hours. The pH is maintained at pH 5.0 by automatically feeding the fermentation medium with 8 M NaOH and 2 M HCl using a feed pump.

The present invention provides a method of increasing the accumulation of pyruvate in microbes through overexpressing wild-type dihydrolipoamide acetyltransferase or mutant dihydrolipoamide acetyltransferases that have a mutation at conservative active sites. The method decreases the intracellular activity of pyruvate dehydrogenase, thus decreases the catabolism and increase the accumulation of pyruvate in microbes. This method leads to increased extracellular accumulation of pyruvate, which can simplify the downstream isolation and purification processes, reduce the production cost and increase the final yield.

Figure 1:
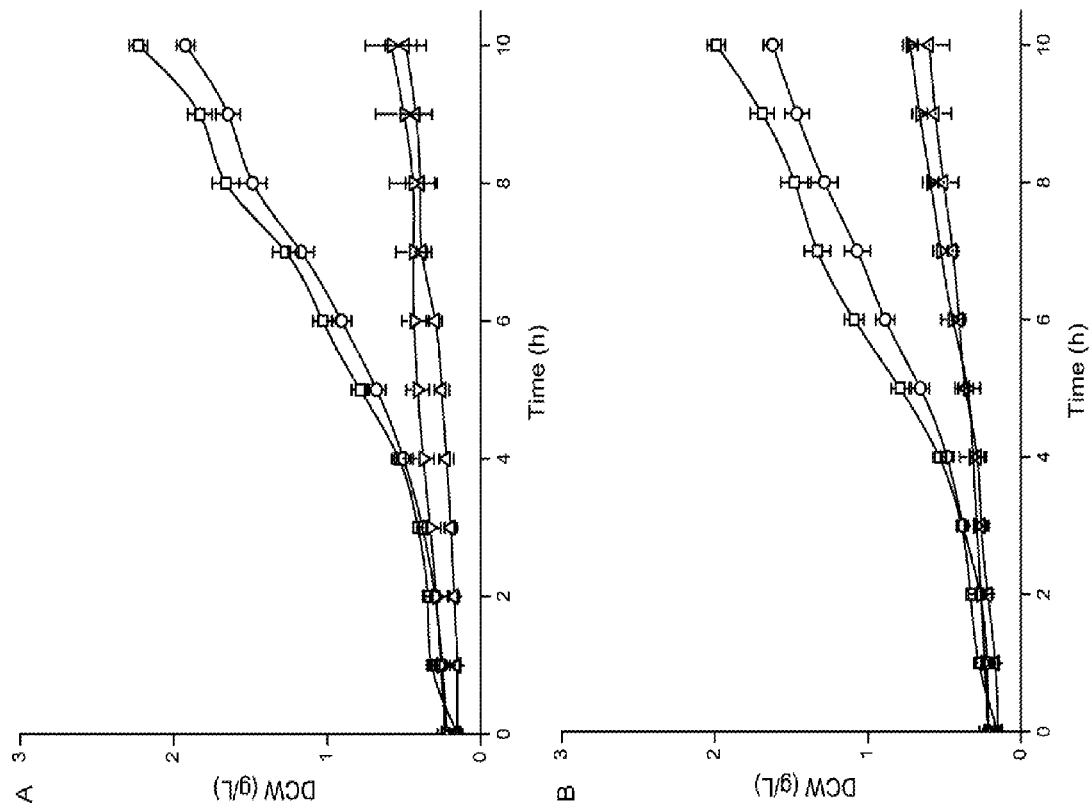
FIG. 1. Cell growth curves. (A) *Y. lipolytica*-WSH Z06 (□), *Y. lipolytica*-C (○), *Y. lipolytica*-409A (Δ), *Y. lipolytica*-413A (∇); (B) *T. glabrata* CCTCC M202019 Δura3 (□), *T. glabrata*-C (○), *T. glabrata*-442A (Δ), *T. glabrata*-446A (∇).

Table 1. Primers used in this invention.

EXAMPLES

Materials and Methods:

YPD medium: 5 g·L$^{-1}$ yeast extract, 10 g·L$^{-1}$ peptone, 10 g·L$^{-1}$ glucose. To make solid medium, add 20 g·L$^{-1}$ Agar. Hygromycin B was added to the concentration of 400 mg·L$^{-1}$ for selection of positive recombinant transformants.

YNB medium: 10 g·L$^{-1}$ glucose, 0.67 g·L$^{-1}$ (NH$_4$)$_2$SO$_4$, pH 6.

Seed medium for *Y. lipolytica*: 20 g·L$^{-1}$ glucose, 10 g·L$^{-1}$ peptone, 1 g·L$^{-1}$ KH$_2$PO$_4$, 0.5 g·L$^{-1}$ MgSO$_4$.7H$_2$O, pH 5.5. To make solid medium, add 20 g·L$^{-1}$ agar.

Fermentation medium for *Y. lipolytica*: 100 g·L$^{-1}$ glycerol, 3 g·L$^{-1}$ (NH$_4$)$_2$SO$_4$, 3 g·L$^{-1}$ KH$_2$PO$_4$, 1.2 g·L$^{-1}$ MgSO$_4$.7H$_2$O, 0.1 g·L$^{-1}$ K$_2$HPO$_4$, 0.5 g·L$^{-1}$ NaCl, 2×10$^{-7}$ g·L$^{-1}$ thiamine pH 5.5. 20 g·L$^{-1}$ CaCO$_3$ was added as a neutralizing agent before inoculation.

Seed medium for *T. glabrata*: 20 g·L$^{-1}$ glucose, 10 g·L$^{-1}$ peptone, 1 g·L$^{-1}$ KH$_2$PO$_4$, 0.5 g·L$^{-1}$ MgSO$_4$.7H$_2$O, pH 5.5. To make solid medium, add 20 g·L$^{-1}$ agar.

Fermentation medium for *T. glabrata*: 120 g·L$^{-1}$ glucose, 7 g·L$^{-1}$ NH$_4$Cl, 5 g·L$^{-1}$ KH$_2$PO$_4$, 0.8 g·L$^{-1}$ MgSO$_4$.7H$_2$O, 6 g·L$^{-1}$ sodium acetate, 4 mg·L$^{-1}$ niacin, 30 μg·L$^{-1}$ thiamine, 100 μg·L$^{-1}$ pyridoxine hydrochloride, 10 μg·L$^{-1}$ biotin, 50 μg·L$^{-1}$ riboflavin, pH 5.0. 20 g·L$^{-1}$ CaCO$_3$ was added as a neutralizing agent before inoculation.

The *Y. lipolytica* WSH-Z06 was obtained from China Center for Type Culture Collection (CCTCC) with CCTCC NO: M20714.

Determination of biomass: dry cell weight (g·L$^{-1}$) =0.223*OD$_{570}$.

Determination of intercellular pyruvate dehydrogenase activity: cells were collected by centrifugation and washed by 0.9% physiological saline. Cell were resuspended in 10 mL buffer solution containing 0.1 mol·L$^{-1}$ KH$_2$PO$_4$—K$_2$HPO$_4$, 1 mmol·L$^{-1}$ EDTA, 0.01 mmol·L$^{-1}$ DTT (pH 7.5). After addition of one volume of acid-washed quartz sand, cells were disrupted using Tissuelyser for 5 minutes, which was followed by centrifuged at 13,000 g for 10 minutes to remove the precipitation. 0.5 ml supernatant was used for the determination of enzyme activity. 3 ml enzyme activity assay system includes 0.5 ml supernatant, 50 mM HEPES, 0.1% Triton X-100, 1.0 mM MgCl$_2$, 5.0 mM pyruvate, 0.2 mM diphosphothiamin, 2.0 mM NAD$^+$ and 0.1 mM CoA, pH 7.4. Concentration change of NADH was determined by measuring OD$_{340}$ at 30° C. 1 U pyruvate dehydrogenase activity is defined as the enzyme needed to generate 1 μmol NADH within one minute.

Determination of intercellular dihydrolipoamide acetyltransferase activity: 3 ml enzyme activity assay system includes 0.5 ml supernatant of cells lysate, 1.19 mM Tris-HCL buffer (pH 8.0), 0.07 mM acetyl phosphate, 0.042 mM 95% ethanol solution of dihydrolipoamide, 0.07 μM CoA, 7 U Phosphate acetyltransferase, 0.83 mM Sodium acetate. Concentration change of S-acetyldihydrolipoamide is determined by measuring OD$_{240}$. 1 U dihydrolipoamide acetyltransferase activity is defined as the enzyme needed to generate 1 μmol S-acetyldihydrolipoamide within one minute.

Determination of extracellular pyruvate concentration: fermentation samples were centrifuged at 13000 g for 5 minutes. The supernatant was diluted 50 times with ultra-pure water and filtered through 0.22 mm filter paper, and pyruvate concentration of the sample was determined using HPLC.

Conditions for HPLC analysis: pyruvate was determined by HPLC (Agilent 1200 series, Santa Clara, Calif.) with a Aminex HPX-87H ion exchange column (300 mm×7.8 mm; Bio-Rad Laboratories Inc., Hercules, Calif.). The mobile phase was 5 mmol·L$^{-1}$ sulfuric acid in distilled, de-ionized water filtered through a 0.22 μm pore size membrane. The mobile phase flow rate was 0.6 mL·min$^{-1}$. The column temperature was maintained at 35° C., and the injection volume was 10 μL. The pyruvate was detected by UV (wavelength at 210 nm) detector.

Transformation of *Y. lipolytica*: A freshly grown single colony was transferred into liquid YPD medium and cultured at 28° C., 200 rpm for overnight. The yeast cells were transferred into new liquid YPD medium by an inoculum size of 10% (v/v), cultured at 28° C., 200 rpm until the OD600=1.2. The cells were collected by centrifugation, and 8×10$^8$ cells·mL$^{-1}$ were resuspended in 8 mL buffer solution (100 mM LiAc, 10 mM DTT, 0.6 M sorbitol, 10 mM Tris-HCL, pH=7.5) and incubated at 30° C. for 30 minutes. Collect cells again by centrifugation and wash the cells by ice-chilled 5 mL 1 M sorbitol solution three times, and were resuspended to the concentration of 10$^{10}$ cell·mL$^{-1}$ in the sorbitol solution. The linearized integrative recombinant plasmid was added to the cell suspension, incubated on ice for 5 mM, and transferred to a ice-chilled 0.2-cm electric rotor. The electroporation shock was performed at 2.5 KV, 25 μF, 200Ω, and 1 mL ice-chilled 1 M sorbitol solution was immediately added afterwards. The mixture was incubated at room temperature for 1 h. For selection of recombinant *Y. lipolytica*, 0.2 mL cells, which have been electrically shocked, were spread on the YPD plates with 400 mg·L$^{-1}$ Hygromycin B, and cultured at 28° C. for 48-72 h. For recombinant *T. glabrata*, 0.2 mL cells, which have been electrically shocked, were spread on the YNB plates and cultured at 28° C. for 48-72 h. The colonies grown on selective plates were further verified by PCR.

Example 1

Effects of Overexpressing Dihydrolipoamide Acetyltransferase or its Mutations on Cell Growth 1. The recombinant *Y. lipolytica* can be constructed using the following method:

The amino acid sequence of the wild type dihydrolipoamide acetyltransferase from *Y. lipolytica* is shown as SEQ ID NO: 1. Conservative amino acids at the active site of the enzyme, His 409 and Asp 413, were mutated into Ala to get mutation H409A and D413A, respectively.

(1) Constructing the integrative expression vector: The amplified open reading frame (ORF) of hph encoding hygromycin phosphotransferase and plasmid p0 are digested using restriction enzyme Stu I and Hind III simultaneously. The digested fragments were ligated to obtain integrative expression vector p0(hph).

(2) Constructing a recombinant expression plasmid: the ORF of LAT1 encoding dihydrolipoamide acetyltransferase was synthesized; ORF of LAT1 and the integrative plasmid p0(hph) were digested by Bam HI and Eco RI simultaneously which was followed by the ligation of the digested fragments to obtain a recombinant expression plasmid p0(hph)-LAT1; Site-directed mutagenesis of conservative active site residue was accomplished using primers H409A-F (SEQ ID:4)/H409A-R (SEQ ID NO:5) and D413A-F (SEQ ID NO:6)/D413A-R (SEQ ID NO:7), respectively. The resulted plasmids were p0(hph)-409A and p0(hph)-413A, respectively.

(3) Transforming the recombinant expression plasmid into *Y. lipolytica* WSH-Z06: The recombinant expression plasmid was linearized and transformed into *Y. lipolytica* WSH-Z06 using electroporation method. Positive transformants *Y. lipolytica*-K, *Y. lipolytica*-409A and *Y. lipolytica*-413A, which overexpress dihydrolipoamide acetyltransferase wild type, mutant H409A and mutant D413A, respectively, are screened using selective plates. The colonies grown on selective plates were further verified by PCR using primers VBF (SEQ ID NO:12)/VBK (SEQ ID NO:13) in Table 1.

The method of constructing plasmid p0 is well documented in Swennen D, Paul M F, Vernis L, Beckerich J M, Fournier A, Gaillardin C. Secretion of active anti-Ras single-chain Fv antibody by the yeasts *Yarrowia lipolytica* and *Kluyveromyces lactis*. Microbiology-Sgm, 2002. 148: 41-50.

*Y. lipolytica*-K, *Y. lipolytica*-409A and *Y. lipolytica*-413A were inoculated into 0.2 ml YPD medium in 96-well plates and cultured at 28° C., 200 rpm for 10 h. Compared with biomass of *Y. lipolytica* WSH-Z06, biomass of the three recombinants, *Y. lipolytica*-K, *Y. lipolytica*-409A and *Y. lipolytica*-413A, was reduced to 86.5%, 22.0% and 26.2%, respectively (FIG. 1A).

The recombinant *T. glabrata* can be constructed using the following method:

The amino acid sequence of the wild type dihydrolipoamide acetyltransferase from *T. glabrata* is shown as SEQ ID NO:2. Conservative residues at the active site of the enzyme, His 442 and Asp 446, are mutated into Ala to get mutation H442A and D446A, respectively.

(1) Constructing a recombinant expression plasmid: Open reading frame (ORF) of the gene LAT1 encoding dihydrolipoamide acetyltransferase was synthesized based on the published nucleotide sequence by NCBI; LAT1 ORF and the integrative plasmid pRS306TEF1 were digested by restriction enzyme Spe I and Bam HI simultaneously which was followed by the ligation of the digested fragments to obtain a recombinant expression plasmid pRS306TEF1-LAT1. Site-directed mutagenesis of conservative active site residue was accomplished using primers H442A-F (SEQ ID NO:8)/H442A-R (SEQ ID NO:9) and D446A-F (SEQ ID NO:10)/D446A-R (SEQ ID NO:11). pRS306TEF1-LAT1 was used as template DNA to get recombinant expression plasmid pRS306TEF1-442A and pRS306TEF1-446A.

(2) Transforming the recombinant expression plasmid into *T. glabrata* CCTCC M202019 Δura3: the recombinant expression plasmid was linearized and transformed into *T. glabrata* CCTCC M202019 Δura3 by electroporation; Positive transformants *T. glabrata*-C, *T. glabrata*-442A and *T. glabrata*-446A, which overexpress dihydrolipoamide acetyltransferase wild type, mutant H442A and mutant D446A, respectively, were screened using selective plates. The colonies grown on selective plates were further verified by PCR using primers VTB (SEQ ID NO:14)/VTC (SEQ ID NO:15) in Table 1.

The method of constructing *T. glabrata* CCTCC M202019 Δura3 is well documented in Zhou J, Dong Z, Liu L, Du G, Chen J. A reusable method for construction of non-marker large fragment deletion yeast auxotroph strains: A practice in *Torulopsis glabrata*. Journal of Microbiological Methods. 2009; 76:70-74.

Compared with biomass of *T. glabrata* CCTCC M202019 Δura3, biomass of the three recombinants, *T. glabrata*-C, *T. glabrata*-442A and *T. glabrata*-446A, were reduced to 81.5%, 30.2% and 36.3%, respectively (FIG. 1B).

Example 2

Effects of Overexpressing Dihydrolipoamide Acetyltransferase or its Mutants on Intracellular Pyruvate Dehydrogenase Activity 1. *Y. lipolytica*

*Y. lipolytica* WSH-Z06, *Y. lipolytica*-K, *Y. lipolytica*-409A and *Y. lipolytica*-413A were inoculated into YPD medium (20/250 mL) and cultured at 28° C., 200 rpm. Cells at logarithmic growth phase were collected, and the intracellular pyruvate dehydrogenase activity was determined.

Figure 2:
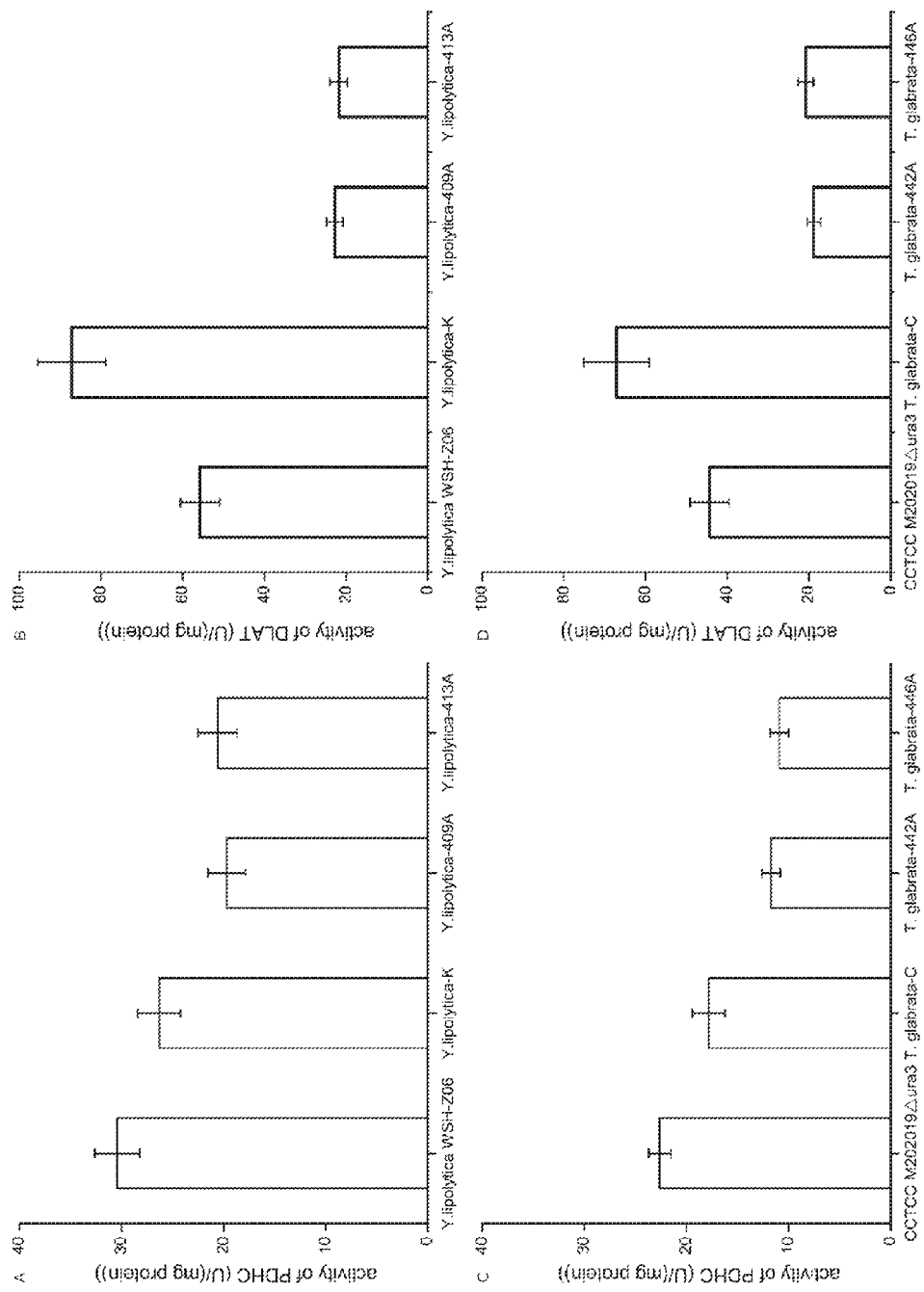
FIG. 2. Activities of pyruvate dehydrogenase and dihydrolipoamide acetyltransferase. (A) intracellular overall activity of pyruvate dehydrogenase complex in recombinant *Y. lipolytica* strains; (B) intracellular dihydrolipoamide acetyltransferase activity in recombinant *Y. lipolytica* strains; (C) intracellular pyruvate dehydrogenase activity of different *T. glabrata* strains; (D) intracellular dihydrolipoamide acetyltransferase activity of different *T. glabrata* strains.

Compared with the intracellular dihydrolipoamide acetyltransferase activity of *Y. lipolytica* WSH-Z06, the activity of dihydrolipoamide acetyltransferase in *Y. lipolytica*-409A and *Y. lipolytica*-413A was reduced to 40.7% and 39.1% respectively, while intracellular dihydrolipoamide acetyltransferase activity of *Y. lipolytica*-K was increased to 256.2% (FIG. 2B).

Compared with the intracellular overall activity of pyruvate dehydrogenase complex in *Y. lipolytica* WSH-Z06, the intracellular overall activity of pyruvate dehydrogenase complex in three recombinants, *Y. lipolytica*-K, *Y. lipolytica*-409A and *Y. lipolytica*-413A, was reduced by 13.5%, 35.2% and 32.2%, to 26.3 U/mg protein, 19.7 U/mg protein and 20.6 U/mg protein, respectively (FIG. 2A).

2. *T. glabrata*

*T. glabrata* CCTCC M202019 Δura3, *T. glabrata*-C, *T. glabrata*-442A and *T. glabrata*-446A were cultured in the same way as *Y. lipolytica* was.

Compared with the intracellular dihydrolipoamide acetyltransferase activity of *T. glabrata* CCTCC M202019 Δura3, the enzyme activity of *T. glabrata*-C was increased to 151.5%, while the intracellular dihydrolipoamide acetyltransferase activity of *T. glabrata*-442A and *T. glabrata*-446A were reduced to 42.3% and 46.7% respectively (FIG. 2D).

Compared with the intracellular pyruvate dehydrogenase activity of *T. glabrata* CCTCC M202019 Δura3, that of *T. glabrata*-C, *T. glabrata*-442A and *T. glabrata*-446A, were reduced by 21.2%, 48.2% and 51.8%, to 17.8 U/mg protein, 11.7 U/mg protein and 10.9 U/mg protein, respectively (FIG. 2C).

Example 3

Effects of Overexpressing Dihydrolipoamide Acetyltransferase or its Mutants on Pyruvate Accumulation

Figure 3:
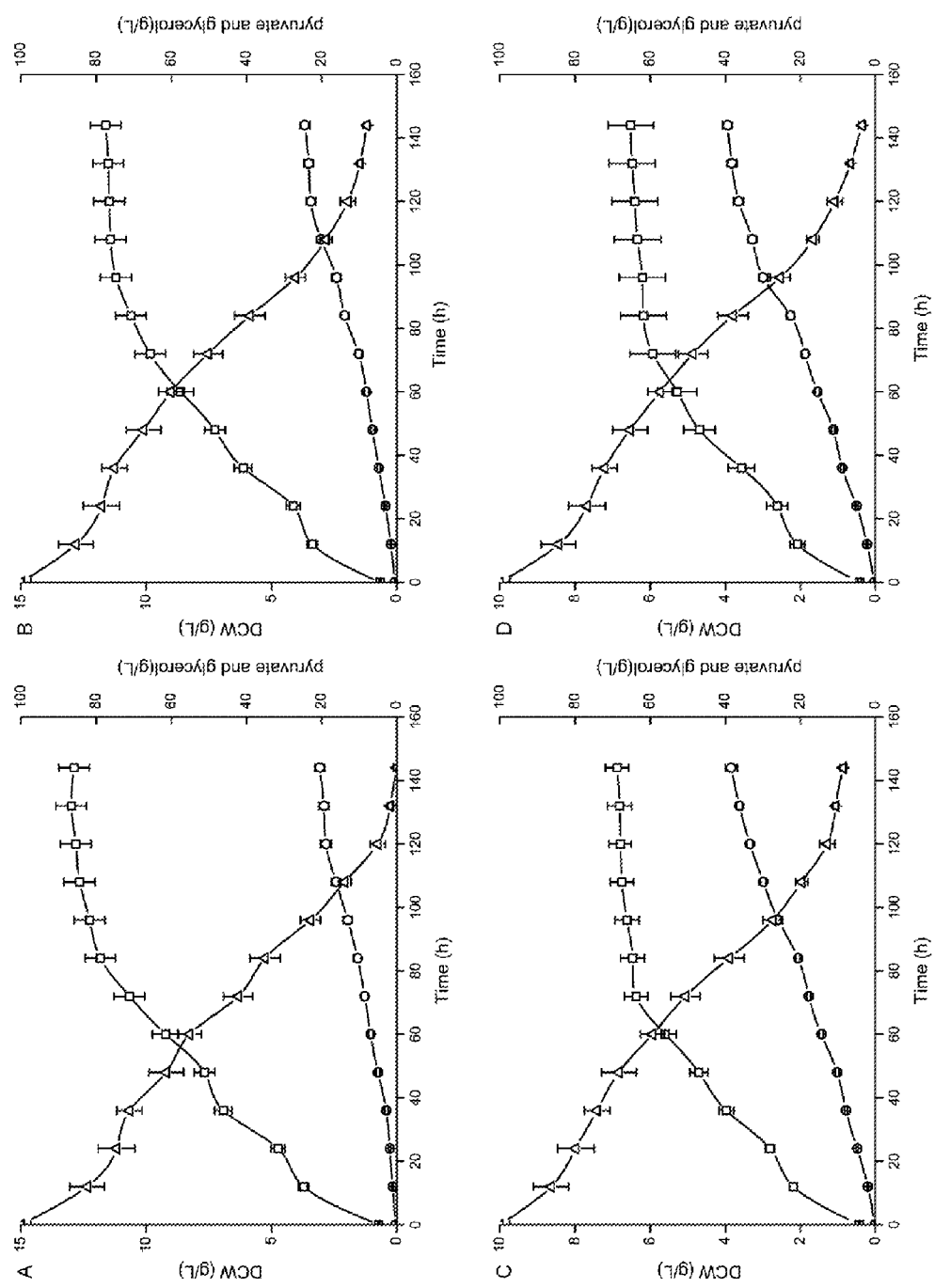
FIG. 3. Extracellular pyruvate concentrations of different *Y. lipolytica* strains; (A) *Y. lipolytica* WSH-Z06, (B) *Y lipolytica*-K, (C) *Y. lipolytica*-409A, (D) *Y. lipolytica*-413A; dry cell weight (□), pyruvate (○), glycerol (Δ).

*Y. lipolytica* WSH-Z06, *Y. lipolytica*-K, *Y. lipolytica*-409A and *Y. lipolytica*-413A were inoculated into fermentation medium (1.5 L medium/3 L fermentor) and cultured at 28° C., 200 rpm for 144 hours. The pyruvate concentration in the supernatant produced by *Y. lipolytica* WSH-Z06, *Y. lipolytica*-K, *Y. lipolytica*-409A and *Y. lipolytica*-413A were 20.5 g·L$^{-1}$, 38.6 g·L$^{-1}$, 38.6 g·L$^{-1}$ and 39.9 g·L$^{-1}$, respectively (FIG. 3). Overexpressing dihydrolipoamide acetyltransferase or its mutations in *Y. lipolytica* WSH-Z06 greatly increased pyruvate yield.

Figure 4:
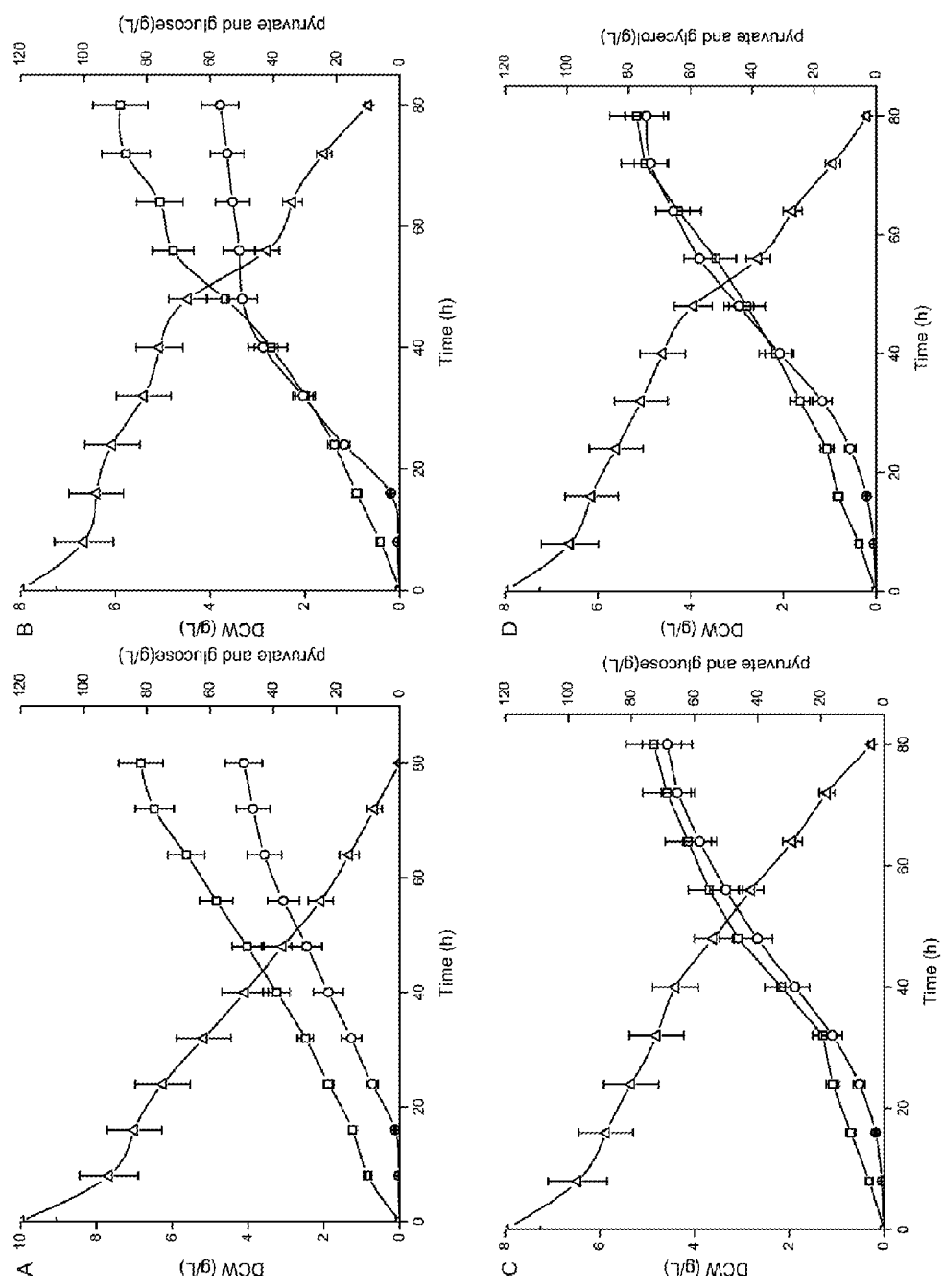
FIG. 4. Extracellular pyruvate concentrations of different *T. glabrata* strains; (A) *T. glabrata* CCTCC M202019 Δura3, (B) *T. glabrata*-C, (C) *T. glabrata*-442A, (D) *T. glabrata*-446A; dry cell weight (□), pyruvate (○), glucose (Δ).

*T. glabrata* CCTCC M202019 Δura3, *T. glabrata*-C, *T. glabrata*-442A and *T. glabrata*-446A were inoculated into fermentation medium (1.5 L medium/3 L fermentor) and cultured at 28° C., 200 rpm for 144 hours. The pyruvate concentration in the supernatant produced by *T. glabrata* CCTCC M202019 Δura3, *T. glabrata*-C, *T. glabrata*-442A and *T. glabrata*-446A were 49.4 g·L$^{-1}$, 56.8 g·L$^{-1}$, 68.6 g·L$^{-1}$ and 74.3 g·L$^{-1}$, respectively (FIG. 4). Overexpressing dihydrolipoamide acetyltransferase or its mutations in *T. glabrata* enormously increased pyruvate yield.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

TABLE 1

Primers used in this invention

| Primers | Sequence (5'-3') |
|---|---|
| H409A-F SEQ ID NO: 4 | CTGACCACCTCTTTCGACGCTCGAGTCGTCG ATGGAGCT |
| H409A-R SEQ ID NO: 5 | AGCTCCATCGACGACTCGAGCGTCGAAAGAG GTGGTCAG |
| D413A-F SEQ ID NO: 6 | TTCGACCACCGAGTCGTCGCTGGAGCTGTTG GAGGCGAG |
| D413A-R SEQ ID NO: 7 | CTCGCCTCCAACAGCTCCAGCGACGACTCGG TGGTCGAA |
| H442A-F SEQ ID NO: 8 | ATAACAGGTACATTTGACGCTAGAACCATTG ACGGTGCT |
| H442A-R SEQ ID NO: 9 | AGCACCGTCAATGGTTCTAGCGTCAAATGTA CCTGTTAT |
| D446A-F SEQ ID NO: 10 | TTTGACCACAGAACCATTGCTGGTGCTAAAG GTGCTGAT |
| D446A-R SEQ ID NO: 11 | ATCAGCACCTTTAGCACCAGCAATGGTTCTG TGGTCAAA |
| VBF SEQ ID NO: 12 | CGTTTGCCAGCCACAGATT |
| VBK SEQ ID NO: 13 | GCAACGGCGACAGAAACG |
| VTB SEQ ID NO: 14 | TGAAGTGGTACGGCGATGC |
| VTC SEQ ID NO: 15 | CACCGTCAATGGTTCTGTGG |

What is claimed is:

1. A genetically engineered microbe strain with enhanced secretion of pyruvate, wherein said microbe strain overexpresses wild type dihydrolipoamide acetyltransferase or dihydrolipoamide acetyltransferase mutant which has mutation at its conservative active site, which is selected from the group consisting of wild type dihydrolipoamide acetyltransferase of SEQ ID NO: 1 or SEQ ID NO: 2, dihydrolipoamide acetyltransferase mutant H409A or D413A of SEQ ID NO: 1, and dihydrolipoamide acetyltransferase mutant H442A or D446A of SEQ ID NO: 2.

2. The genetically engineered microbe strain of claim 1, wherein said microbe strain is *Y. lipolytica*.

3. The genetically engineered microbe strain of claim 2, wherein the amino acid sequence of said wild type dihydrolipoamide acetyltransferase is SEQ ID NO: 1.

4. The genetically engineered microbe strain of claim 3, wherein said mutation at conservative active site of said dihydrolipoamide acetyltransferase mutant is H409A or D413A.

5. The genetically engineered microbe strain of claim 1, wherein said genetically engineered microbe strain is constructed as follows:
(1) Constructing an integrative expression vector: the gene hph encoding hygromycin phosphotransferase and plasmid p0 are digested at the same time using restriction enzyme Stu I and Hind III; The digested fragments are connected to obtain the integrative expression vector p0(hph);

(2) Constructing a recombinant expression plasmid: The open reading frame of the gene LAT1 encoding dihydrolipoamide acetyltransferase is synthesized; The LAT1 ORF and the integrative plasmid p0(hph) are digested by restriction enzyme Bam HI and Eco RI simultaneously which is followed by the ligation of the digested fragments to obtain a recombinant expression plasmid p0(hph)-LAT1; Site-directed mutagenesis is accomplished using primers H409A-F/H409A-R and D413A-F/D413A-R; p0(hph)-LAT1 is used as template DNA to get recombinant expression plasmid p0(hph)-409A and p0(hph)-413A;

(3) Transforming the recombinant expression plasmid into *Y. lipolytica* WSH-Z06: The recombinant expression plasmid p0(hph)-LAT1, p0(hph)-409A or p0(hph)-413A is linearized and transformed into *Y. lipolytica* WSH-Z06 by electroporation; positive transformants *Y. lipolytica*-K, *Y. lipolytica*-409A and *Y. lipolytica*-413A, which overexpress dihydrolipoamide acetyltransferase wild type, H409A mutant and D413A mutant, respectively, are screened and verified.

6. The genetically engineered microbe strain of claim 1, wherein said genetically engineered microbe strain is *T. glabrata*.

7. The genetically engineered microbe strain of claim 6, wherein the amino acid sequence of said wild type dihydrolipoamide acetyltransferase is SEQ ID NO: 2.

8. The genetically engineered microbe strain of claim 7, wherein said mutation at conservative active site of said dihydrolipoamide acetyltransferase mutant is H442A or D446A.

9. The genetically engineered microbe strain of claim 6, wherein said genetically engineered microbe strain is constructed as follows:
(1) Constructing a recombinant expression plasmid: The open reading frame of the gene LAT1 encoding dihydrolipoamide acetyltransferase is synthesized; The LAT1 ORF and the integrative plasmid pRS306TEF1 are digested by restriction enzyme Spe I and Bam HI simultaneously which is followed by the ligation of the digested fragments to obtain a recombinant expression plasmid pRS306TEF1-LAT1; Site-directed mutagenesis is accomplished using primers H442A-F/H442A-R and D446A-F/D446A-R; pRS306TEF1-LAT1 is used as template DNA to get recombinant expression plasmid pRS306TEF1-442A and pRS306TEF1-446A;
(2) Transforming the recombinant expression plasmid into *T. glabrata* CCTCC M202019 Δura3: The recombinant expression plasmid pRS306TEF1-LAT1, pRS306TEF1-442A or pRS306TEF1-446A is linearized and transformed into *T. glabrata* CCTCC M202019 Δura3 by electroporation; positive transformants *T. glabrata*-C, *T. glabrata*-442A and *T. glabrata*-446A, which overexpress dihydrolipoamide acetyltransferase wild type, H442A mutant and D446A mutant, respectively, are screened and verified.

* * * * *

SEQUENCE LISTING

<160> NUMBER OF SEQ ID NOS: 15

<210> SEQ ID NO 1
<211> LENGTH: 436
<212> TYPE: PRT
<213> ORGANISM: Yarrowia lipolytica

<400> SEQUENCE: 1

Met Thr Gln Gly Asn Ile Gly Ala Trp Gln Lys Ser Val Gly Asp Ala
1               5                   10                  15

Leu Ala Pro Gly Glu Val Leu Val Glu Ile Glu Thr Asp Lys Ala Gln
                20                  25                  30

Met Asp Phe Glu Phe Gln Asp Gly Tyr Leu Ala Lys Ile Leu Leu
            35                  40                  45

Asp Ala Gly Ala Lys Asp Ile Ala Val Gly Thr Pro Ile Gly Val Tyr
        50                  55                  60

Val Glu Asp Glu Ala Asp Val Ala Ala Phe Lys Asp Phe Thr Ile Asp
65                  70                  75                  80

Asp Ala Gly Gly Val Pro Lys Pro Pro Lys Thr Glu Glu Gln Lys Glu
                85                  90                  95

Glu Glu Glu Tyr Glu Ala Glu Lys Ala Glu Lys Ala Glu Lys Glu Ala
            100                 105                 110

Glu Ala Ser Lys Glu Thr Ala Ser Pro Ala Pro Ser Ser Gln Ser Ser
        115                 120                 125

Ala Pro Ala Ala Pro Thr Pro Pro Ser Ser Arg Ile Phe Ala Ser Pro
    130                 135                 140

Met Ala Lys Thr Ile Ala Leu Glu Lys Gly Ile Lys Leu Ser Glu Ile
145                 150                 155                 160

```
Lys Gly Ser Gly Pro Gly Gly Arg Ile Ile Lys Arg Asp Val Glu Asn
            165                 170                 175

Trp Thr Pro Pro Ala Ala Pro Ala Ala Lys Ala Ala Pro Ala Lys Gly
        180                 185                 190

Ala Ala Pro Ala Ala Ala Ala Ala Gly Ser Ala Tyr Thr Asp Ile
            195                 200                 205

Pro Leu Thr Asn Met Arg Lys Thr Ile Ala Ser Arg Leu Thr Gln Ser
        210                 215                 220

Lys Asn Thr Ser Pro Asp Tyr Ile Val Ser Thr Val Ser Val Ser
225                 230                 235                 240

Lys Leu Leu Lys Leu Arg Ala Ala Leu Asn Ala Ser Ser Asp Gly Thr
            245                 250                 255

Tyr Lys Leu Ser Ile Asn Asp Leu Leu Val Lys Ala Leu Ala Val Ala
            260                 265                 270

Asn Thr Lys Val Pro Gln Val Asn Ser Gln Trp Leu Glu Ser Glu Gly
            275                 280                 285

Val Ile Arg Gln Phe Thr Asn Val Asp Val Ser Val Ala Thr
            290                 295                 300

Pro Thr Gly Leu Ile Thr Pro Val Val Lys Asn Ala Asn Leu Lys Gly
305                 310                 315                 320

Leu Ala Glu Ile Ser Lys Glu Ile Lys Ala Leu Gly Lys Lys Ala Lys
            325                 330                 335

Asp Gly Lys Leu Ala Pro Glu Glu Tyr Gln Gly Gly Thr Val Thr Ile
            340                 345                 350

Ser Asn Leu Gly Met Asn His Ala Val Ser Phe Phe Thr Ala Ile Ile
            355                 360                 365

Asn Pro Pro Gln Ala Ala Ile Leu Ala Val Gly Thr Thr Glu Arg Lys
            370                 375                 380

Ala Ile Glu Asp Val Asp Ser Glu Ala Gly Phe Val Phe Asp Val
385                 390                 395                 400

Val Thr Leu Thr Thr Ser Phe Asp His Arg Val Val Asp Gly Ala Val
            405                 410                 415

Gly Gly Glu Trp Val Lys Ala Leu Lys Gln Val Val Glu Asn Pro Ile
            420                 425                 430

Glu Met Leu Leu
        435

<210> SEQ ID NO 2
<211> LENGTH: 469
<212> TYPE: PRT
<213> ORGANISM: Torulopsis glabrata

<400> SEQUENCE: 2

Met Ser Ala Leu Leu Arg Ala Leu Pro Gln Val Ser Arg Thr Ala Leu
1               5                   10                  15

Arg Gly Arg Leu Val Thr Pro Met Thr Leu Arg Leu Tyr Ala Ser Phe
            20                  25                  30

Pro Pro His Thr Val Ile Gly Met Pro Ala Leu Ser Pro Thr Met Ser
        35                  40                  45

Gln Gly Asn Leu Ala Val Trp Ser Lys Lys Glu Gly Asp Ser Leu Ala
    50                  55                  60

Pro Gly Asp Val Leu Ala Glu Ile Glu Thr Asp Lys Ala Gln Met Asp
65              70                  75                  80

Phe Glu Phe Gln Asp Glu Gly Tyr Leu Ala Lys Ile Leu Val Pro Ala
                85                  90                  95
```

Gly Thr Lys Asp Val Ala Val Ser Arg Pro Ile Ala Val Tyr Val Glu
            100                 105                 110

Asp Glu Ala Asp Val Ala Ala Phe Lys Asp Phe Thr Val Glu Asp Ala
        115                 120                 125

Gly Gly Ser Gln Ser Ser Ala Pro Ala Ala Glu Glu Gln Lys Glu
    130                 135                 140

Glu Pro Lys Lys Glu Val Lys Glu Lys Ser Glu Lys Lys Ala
145                 150                 155                 160

Ala Lys Ser Asn Ser Thr Pro Ser Ser Val Ala Ser Gly Asp Arg Ile
                165                 170                 175

Ile Ala Ser Pro Leu Ala Lys Thr Ile Ala Leu Glu Lys Gly Ile Ala
            180                 185                 190

Leu Lys Ser Val Lys Gly Thr Gly Pro Arg Gly Arg Ile Thr Lys Ala
        195                 200                 205

Asp Val Glu Lys Tyr Leu Glu Ser Ala Pro Lys Ser Thr Ser Thr Ala
    210                 215                 220

Ala Pro Ser Ala Thr Pro Ser Thr Thr Gly Gly Ala Ser Tyr Glu Asp
225                 230                 235                 240

Leu Glu Ile Thr Asn Met Arg Gln Ile Ile Gly Asp Arg Leu Leu Gln
                245                 250                 255

Ser Arg Gln Ser Ile Pro Ser Tyr Ile Val Ser Ser Asp Ile Ser Val
            260                 265                 270

Ser Lys Leu Leu Lys Leu Arg Lys Ser Leu Asn Ala Thr Ala Lys Asp
        275                 280                 285

Gln Tyr Lys Leu Ser Ile Asn Asp Ile Leu Ile Lys Ala Val Thr Val
    290                 295                 300

Ala Ala Arg Arg Val Pro Asp Ala Asn Ser Tyr Trp Leu Gln Asn Glu
305                 310                 315                 320

Gly Ile Ile Arg Gln Phe Lys Asn Val Asp Val Ser Val Ala Val Ala
                325                 330                 335

Thr Pro Thr Gly Leu Leu Thr Pro Ile Val Lys Asn Ala Glu Ser Lys
            340                 345                 350

Gly Leu Ile Glu Ile Ser Lys Glu Val Lys Glu Leu Ala Ser Arg Ala
        355                 360                 365

Lys Ile Asn Lys Leu Val Pro Glu Glu Phe Gln Gly Gly Thr Ile Cys
    370                 375                 380

Ile Ser Asn Leu Gly Met Asn Pro Ala Val Ser Met Phe Thr Ser Ile
385                 390                 395                 400

Ile Asn Pro Pro Gln Ser Thr Ile Leu Ala Ile Gly Thr Val Lys Arg
                405                 410                 415

Val Ala Val Glu Asp Ala Gly Glu Asn Gly Ile Ala Phe Asp Asp
            420                 425                 430

Gln Val Thr Ile Thr Gly Thr Phe Asp His Arg Thr Ile Asp Gly Ala
        435                 440                 445

Lys Gly Ala Asp Phe Met Arg Glu Leu Lys Thr Val Ile Glu Asn Pro
    450                 455                 460

Leu Gln Leu Leu Leu
465

<210> SEQ ID NO 3
<211> LENGTH: 1596
<212> TYPE: DNA
<213> ORGANISM: Artificial
<220> FEATURE:

<223> OTHER INFORMATION: php Vector

<400> SEQUENCE: 3

| | | |
|---|---|---|
| gagcaccgcc gccgcaagga atggtgcatg ctgaggtgtc tcacaagtgc cgtgcagtcc | 60 | |
| cgcccccact tgcttctctt tgtgtgtagt gtacgtacat tatcgagacc gttgttcccg | 120 | |
| cccacctcga tccggcatgc tgaggtgtct cacaagtgcc gtgcagtccc gcccccactt | 180 | |
| gcttctcttt gtgtgtagtg tacgtacatt atcgagaccg ttgttcccgc ccacctcgat | 240 | |
| ccggcatgct gaggtgtctc acaagtgccg tgcagtcccg ccccacttg cttctctttg | 300 | |
| tgtgtagtgt acgtacatta tcgagaccgt tgttcccgcc cacctcgatc cggcatgctg | 360 | |
| aggtgtctca caagtgccgt gcagtcccgc ccccacttgc ttctctttgt gtgtagtgta | 420 | |
| cgtacattat cgagaccgtt gttcccgccc acctcgatcc ggcatgcact gatcacgggc | 480 | |
| aaaagtgcgt atatatacaa gagcgtttgc cagccacaga ttttcactcc acacaccaca | 540 | |
| tcacacatac aaccacacac atccacaatg aaaaagcctg aactcaccgc gacgagcgtc | 600 | |
| gagaagtttc tgatcgaaaa gttcgacagc gtctccgacc tgatgcagct ctcggagggc | 660 | |
| gaagaatctc gtgctttcag cttcgatgta ggagggcgtg gatatgtcct gcgggtaaat | 720 | |
| agctgcgccg atggtttcta caaagatcgt tatgtttatc ggcactttgc atcggccgcg | 780 | |
| ctcccgattc cggaagtgct tgacattggg gagttcagcg agagcctgac ctattgcatc | 840 | |
| tcccgccgtg cacagggtgt cacgttgcaa gacctgcctg aaaccgaact gcccgctgtt | 900 | |
| ctgcagccgg tcgcggaggc catggatgcg atcgctgcgg ccgatcttag ccagacgagc | 960 | |
| gggttcggcc cattcggacc gcaaggaatc ggtcaataca ctacatggcg tgatttcata | 1020 | |
| tgcgcgattg ctgatcccca tgtgtatcac tggcaaactg tgatggacga ccgtcagt | 1080 | |
| gcgtccgtcg cgcaggctct cgatgagctg atgctttggg ccgaggactg ccccgaagtc | 1140 | |
| cggcacctcg tgcacgcgga tttcggctcc aacaatgtcc tgacggacaa tggccgcata | 1200 | |
| acagcggtca ttgactggag cgaggcgatg ttcggggatt cccaatacga ggtcgccaac | 1260 | |
| atcttcttct ggaggccgtg gttggcttgt atggagcagc agacgcgcta cttcgagcgg | 1320 | |
| aggcatccgg agcttgcagg atcgccgcgg ctccgggcgt atatgctccg cattggtctt | 1380 | |
| gaccaactct atcagagctt ggttgacggc aatttcgatg atgcagcttg gcgcagggt | 1440 | |
| cgatgcgacg caatcgtccg atccggagcc gggactgtcg gcgtacaca aatcgcccgc | 1500 | |
| agaagcgcgg ccgtctggac cgatggctgt gtagaagtac tcgccgatag tggaaaccga | 1560 | |
| cgccccagca ctcgtccgag ggcaaaggaa tagtcg | 1596 | |

<210> SEQ ID NO 4
<211> LENGTH: 39
<212> TYPE: DNA
<213> ORGANISM: Artificial
<220> FEATURE:
<223> OTHER INFORMATION: H409A-F Primer

<400> SEQUENCE: 4

| | |
|---|---|
| ctgaccacct ctttcgacgc tcgagtcgtc gatggagct | 39 |

<210> SEQ ID NO 5
<211> LENGTH: 39
<212> TYPE: DNA
<213> ORGANISM: Artificial
<220> FEATURE:
<223> OTHER INFORMATION: H409A-R Primer

<400> SEQUENCE: 5
agctccatcg acgactcgag cgtcgaaaga ggtggtcag                                  39

<210> SEQ ID NO 6
<211> LENGTH: 39
<212> TYPE: DNA
<213> ORGANISM: Artificial
<220> FEATURE:
<223> OTHER INFORMATION: D413A-F Primer

<400> SEQUENCE: 6
ttcgaccacc gagtcgtcgc tggagctgtt ggaggcgag                                  39

<210> SEQ ID NO 7
<211> LENGTH: 39
<212> TYPE: DNA
<213> ORGANISM: Artificial
<220> FEATURE:
<223> OTHER INFORMATION: D413A-R Primer

<400> SEQUENCE: 7
ctcgcctcca acagctccag cgacgactcg gtggtcgaa                                  39

<210> SEQ ID NO 8
<211> LENGTH: 39
<212> TYPE: DNA
<213> ORGANISM: Artificial
<220> FEATURE:
<223> OTHER INFORMATION: H442A-F Primer

<400> SEQUENCE: 8
ataacaggta catttgacgc tagaaccatt gacggtgct                                  39

<210> SEQ ID NO 9
<211> LENGTH: 39
<212> TYPE: DNA
<213> ORGANISM: Artificial
<220> FEATURE:
<223> OTHER INFORMATION: H442-A-R Primer

<400> SEQUENCE: 9
agcaccgtca atggttctag cgtcaaatgt acctgttat                                  39

<210> SEQ ID NO 10
<211> LENGTH: 39
<212> TYPE: DNA
<213> ORGANISM: Artificial
<220> FEATURE:
<223> OTHER INFORMATION: D446A-F Primer

<400> SEQUENCE: 10
tttgaccaca gaaccattgc tggtgctaaa ggtgctgat                                  39

<210> SEQ ID NO 11
<211> LENGTH: 39
<212> TYPE: DNA
<213> ORGANISM: Artificial
<220> FEATURE:
<223> OTHER INFORMATION: D446A-R Primer

<400> SEQUENCE: 11
atcagcacct ttagcaccag caatggttct gtggtcaaa                                  39

<210> SEQ ID NO 12
<211> LENGTH: 19
<212> TYPE: DNA

```
<213> ORGANISM: Artificial
<220> FEATURE:
<223> OTHER INFORMATION: VBF Primer

<400> SEQUENCE: 12
cgtttgccag ccacagatt                                              19

<210> SEQ ID NO 13
<211> LENGTH: 18
<212> TYPE: DNA
<213> ORGANISM: Artificial
<220> FEATURE:
<223> OTHER INFORMATION: VBK Primer

<400> SEQUENCE: 13
gcaacggcga cagaaacg                                               18

<210> SEQ ID NO 14
<211> LENGTH: 19
<212> TYPE: DNA
<213> ORGANISM: Artificial
<220> FEATURE:
<223> OTHER INFORMATION: VTB Primer

<400> SEQUENCE: 14
tgaagtggta cggcgatgc                                              19

<210> SEQ ID NO 15
<211> LENGTH: 20
<212> TYPE: DNA
<213> ORGANISM: Artificial
<220> FEATURE:
<223> OTHER INFORMATION: VTC Primer

<400> SEQUENCE: 15
caccgtcaat ggttctgtgg                                             20
```